United States Patent [19]

Kennedy

[11] 4,106,495
[45] Aug. 15, 1978

[54] VECTORCARDIOGRAPHIC METHOD FOR AMBULATORY PATIENTS

[75] Inventor: Harold L. Kennedy, Baltimore, Md.

[73] Assignee: Del Mar Avionics, Irvine, Calif.

[21] Appl. No.: 786,252

[22] Filed: Apr. 11, 1977

[51] Int. Cl.² .............................................. A61B 5/04
[52] U.S. Cl. ............................................... 128/2.06 V
[58] Field of Search ................... 128/2.06 B, 2.06 E, 128/2.06 G, 2.06 R, 2.06 V

[56] References Cited

U.S. PATENT DOCUMENTS

| | | | |
|---|---|---|---|
| 3,221,334 | 11/1965 | Jones, Jr. | 128/2.06 G |
| 3,509,878 | 5/1970 | Shaw | 128/2.06 V |
| 3,534,727 | 10/1970 | Roman | 128/2.06 E |
| 3,934,267 | 1/1976 | Kosaka | 128/2.06 G |
| 3,991,747 | 11/1976 | Stanly et al. | 128/2.06 E |
| 4,006,737 | 2/1977 | Cherry | 128/2.06 G |

Primary Examiner—William E. Kamm
Attorney, Agent, or Firm—George F. Smyth

[57] ABSTRACT

A method of obtaining a continuous sequence of horizontal vectorcardiograms from an ambulatory patient throughout a 24-hour period. A simplified five-electrode ECG lead system is affixed to the patient and the ECG signals are recorded on a portable magnetic tape recorder attached to the patient. Thereafter, the tape is removed from the recorder and taken to a processing station for playback, display, and analysis. The tape is played back at high speed to permit rapid scanning of the tape for anomalies in the vectorcardiograph. Anomalies can then be studied in detail by playing back the tape at a reduced speed. The vectorcardiographs exhibit high correlation with those obtained by use of the more common, but more complex, Frank lead system.

7 Claims, 9 Drawing Figures

VECTORCARDIOGRAPHIC METHOD FOR AMBULATORY PATIENTS

BACKGROUND OF THE INVENTION

1. Field of the Invention

The present invention is in the field of cardiology, and more specifically is a method for obtaining a continuous sequence of horizontal vectorcardiograms from an ambulatory patient over an extended interval of time by use of a five-electrode lead system.

2. Description of the Prior Art

Since its introduction in 1949, the concept of dynamic portable monitoring of cardiac performance has grown widely. Modern technology in the form of Holter recording systems was introduced in 1961 and now provides more than 24-hours of continuous electrocardiographic data. The Holter technique was disclosed by Holter in a paper entitled "New Method for Heart Studies" in Science, Vol 134, pp 1214-1220 (1961). More recently, ambulatory monitoring and recording techniques have been adapted to recording ambulatory blood pressure and continuous electroencephalograms. From this relatively rapidly changing technology in Holter recording has emerged the innovation disclosed herein of deriving a horizontal plane vectorcardiogram from a two-channel Holter recording of electrocardiographic data. Such derived adjunctive data enhances the clinical utility of routine ambulatory electrocardiography.

Since the inception of dynamic ambulatory electrocardiography procedures, Holter recording examination has been performed utilizing a two-channel lead system employing a modified chest $V_1$ lead and a chest bipolar lead $V_5$. This lead system was specifically chosen to facilitate diagnosis and identification of cardiac dysrhythmias, particularly anomalous extrasystoles, as seen in lead $V_1$, and to best detect left ventricular myocardial ischemia by employing a commonly used sensitive exercise lead, chest bipolar $V_5$. Early investigations of anomalous extrasystoles sought to interpret the simultaneous analog electrocardiographic signals derived from this $V_1$ and $V_5$ lead system, and led to a search for some way to integrate or combine these two channels of electrocardiographic data. The present invention grew out of this long-felt need.

Vectorcardiogram studies using magnetic tape recordings to display the inscription of the vector in slow motion have been previously reported in a paper "Time Exapnsion in Vectorcardiography: the advantages of Magnetic Tape Recording" by Estes, et al. in American Heart Journal Vol. 63, pp. 98-100 (1962). These studies used the Frank lead system or a modified McFee lead system, and were designed to measure horizontal (X), longitudinal (Y), and saggital (Z) plane forces. Much of the merit of the present procedure resides in the simplification achieved by deriving the horizontal plane vectorcardiogram from commonly used electrocardiographic $V_1$ and $V_5$ data. This adjunctive vectorcardiographic data complements the analog electrocardiographic $V_1$ and $V_5$ signal data by providing a visual integrated picture of those simultaneous signals.

Previous studies have already indicated merit in the vectorcardiographic analysis of anomalous and ectopic beats for identifying the site of origin of ectopic beats. These descriptions, however, have not gained wide clinical interest. This lack of interest may in part be due to the relatively large number of electrodes necessitated by standard vectorcardiographic methods, and the possible difficulty in some instances of recording chance ectopic beats on standard vectorcardiographic methods. Accordingly, clinicians generally seem less inclined to seek and utilize X, Y and Z axis analog data in the routine management of patients.

SUMMARY OF THE INVENTION

The Holter horizontal plane vectorcardiogram methodology in a practical sense, overcomes these impediments. Its simplicity of permitting easy horizontal plane vectorcardiographic examination of any ectopic beat which may occur during a 24-hour period, combined with the feature that such data is adjunctively derived from the useful and clinically familiar standard $V_1$ and $V_5$ electrocardiographic data, make it an attractive adjunctive method of investigation.

Some important practical advantages of Holter horizontal plane vectorcardiograms in the interpretation of ambulatory electrocardiographic recordings are evident and have already been appreciated. MOst noteworthy, has been the contribution of this technique to the recognitiion and study of anomalous or ectopic beats. Whereas visual inspection of analog electrocardiographic signals for recognition of anomalous beats from sinus beats has been somewhat enhanced by two-channel electrocardiograhic recordings, this visual discrimination is immeasurably facilitated by the display and comparison of those analog electrocardiographic signals in the form of Holter horizontal plane vectorcardiograms.

Such anomalous beats not only commonly result in alteration of the readily apparent direction and magnitude of QRS and T force vectors, but also affect the direction of rotation of QRS vector forces, often accompanied by abnormal delays of QRS vector inscription. The latter characteristics are not readily apparent in analog electrocardiographic signals, and give additional discriminative data. Thus, the potential adaptation of using Holter horizontal vectorcardiograms in the high-speed analysis and interpretation of ambulatory electrocardiographic data offers an additional or adjunctive method of recognition of anomalous or ectopic beats.

The surprising similarity of the derived Holter horizontal plane vectorcardiogram to Frank horizontal plane vectorcardiograms is a fortuitous and fortunate discovery, for it suggests the hypothesis that extant Frank horizontal plane vectorcardiographic data may be applicable to interpretation of Holter horizontal plane vectorcardiograms. This similarity between Holter and Frank horizontal plane vectorcardiograms has been found in a preliminary manner to exist for a variety of cardiac disorders of impulse formation and conduction (e.g. ventricular ectopic beats and bundle branch block).

In the present invention, bipolar lead $V_5$ is so oriented, due to electrode placement, as to be adaptable to measure to X axis vector forces of the horizontal plane. Similarly,, modified chest bipolar lead $V_1$, owing to the placement of the negative electrode just inferior to the outer one-third of the clavicle provides a measurement of electrocardiographic signals of the Z axis vector forces of the horizontal plane of the body. However, the polarity of this measured modified chest lead $V_1$ must be reversed, to be adaptable as a Z axis vector force of the horizontal plane of the body for similarity to the Frank lead system. These bipolar electrocardiographic signals $V_1$ and $V_5$ provide a modified measurement of the Z and X vector forces of the horizontal plane, respectively.

The $V_1$ and $V_5$ signals are recorded on a portable magnetic tape recorder which is affixed to the patient, who goes about his daily activities, including programmed exercises, with minimal impediment. The recorder used in a preferred embodiment is capable of recording 24 continuous hours of the $V_1$ and $V_5$ signals. The $V_1$ and $V_5$ signals are recorded simultaneously on two separate tracks of a magnetic tape with insurance of correct phasing of the recorded signals.

The recording thus obtained is played back for analysis on a playback unit capable of simultaneously reproducing the signals recorded in the two tracks of the tape.

The reproduced $V_1$ and $V_5$ signals produced by the playback unit are applied simultaneously to orthogonal input terminals of a display device, such as a cathode ray tube, which produces a visual display of the vector whose components are the $V_1$ and $V_5$ signals.

During recording, the tape is moved past the recording heads at a relatively slow speed to permit recordings of long duration. Upon subsequent playback, the tape is moved more rapidly past the pick-up heads to permit scanning of the entire recording in a matter of minutes. During playback, the vector display is closely observed with respect to normal or cardiac electrical activity.

Successive vectorcardiograms are inscribed on the display in rapid succession like the successive frames of a motion picture. Typically, a large number of successive vectorcardiograms will have substantially the same size and shape, and will therefore be substantially congruent on the display. These substantially congruent vectorcardiograms define a normal or base mode of heart action against which deviant action is readily discernable as a variation in the shape of the displayed deviant vectorcardiogram.

Once the occurrence of deviant action has been established a portion of the tape may be played again at slower speed to permit detailed observation and analysis of the deviant vectorcardiogram.

In one embodiment of the invention, conventional electrocardiographic charts are automatically plotted by a plotter. These charts, which show the $V_1$ and $V_5$ signals versus time are a useful adjunct to the vector display to facilitate interpretation and diagnosis.

The novel features which are believed to be characteristic of the invention, both as to organization and method of operation, together with further objects and advantages thereof, will be better understood from the following description considered in connection with the accompanying drawings in which several preferred embodiments of the invention are illustrated by way of example.

BRIEF DESCRIPTION OF THE DRAWINGS

FIG. 1, including

DESCRIPTION OF THE PREFERRED EMBODIMENT

Figure 1A:
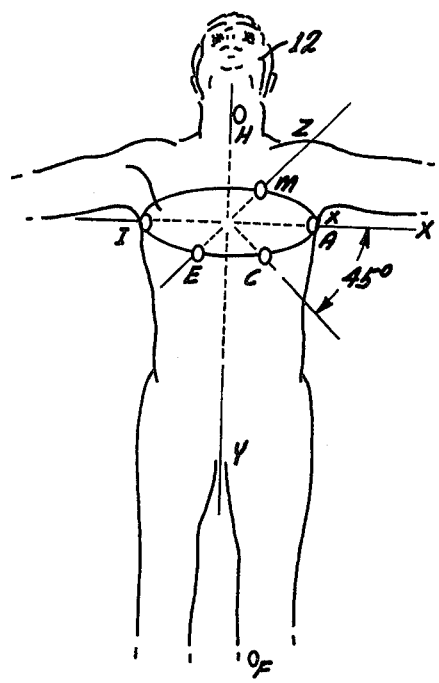
FIGS. 1a and 1b are diagrams illustrating the prior art and showing respectively the placement of the electrodes in the Frank lead system and the resistance network used with the Frank electrodes.
Figure 1B:
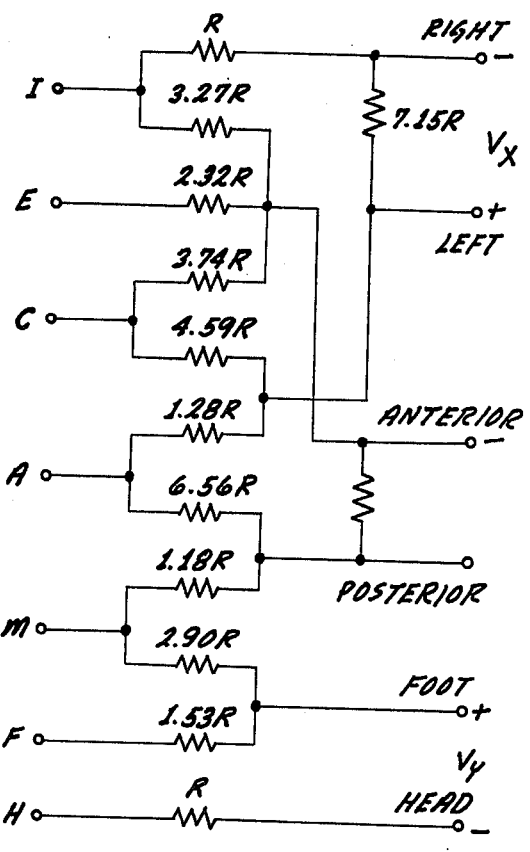

Turning now to the figures, FIG. 1, including FIGS. 1a and 1b illustrate a prior art system for positioning the electrodes on the body of the patient. Specifically, FIG. 1a shows the placement of the electrodes on the body of the patient 12 in the corrected orthogonal Frank lead system. This system is probably the most popular of the systems used in vectorcardiography. In accordance with the conventional nomenclature used, the electrodes are designated by letters.

In the Frank system, seven electrodes, designated as H, F, I, E, C, A, M are applied to the body at the following locations:

H: Forehead or neck

F: Left leg

I, E, C, A, M are located along the same transverse level: The fourth intercostal space if the patient is supine, or the fifth intercostal space if the patient is sitting.

I: Anterior axillary line

E: Center of Sternum

A: Left anterior axillary line

C: At a 45° angle between E and A

M: Center of spine.

The electrodes attached at the positions shown in FIG. 1a are connected to a resistance network as shown in FIG. 1b. In effect, the resistance network alters the magnitudes of the signals sensed by various of the electrodes to produce outputs $V_x$, $V_y$, and $V_z$ of normalized magnitude relative to the X, Y, and Z axes shown in FIG. 1a. If the $V_x$ and $V_z$ signals are chosen for display, the display will show the projection of the vector force on the horizontal (X-Z) plane. Similiarly, if the $V_y$ and $V_z$ are chosen for display, the display will show the projection of the vector force in the left sagittal (Y-Z) plane, and if the $V_x$ and $V_y$ signals are chosen for display, the display will show the projection of the force vector in the frontal (X-Y) plane of FIG. 1a. In practice, all seven electrodes are affixed to the patient, even if it is known in advance that only one of the projections is desired. Normally, however, all three projections are used to envision the spacial orientation of the force vector.

Figure 2:
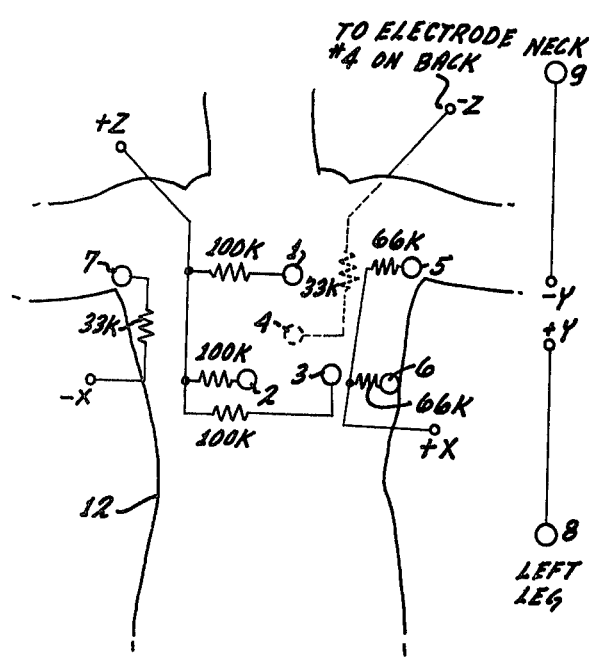
FIG. 2 is a diagram illustrating the prior art and showing placement of the electrodes in the McFee-Parungao lead system and the associated resistance network.

FIG. 2 shows the placement of the electrodes in another lead system, known as the McFee-Parungao system. This prior art system employs nine electrodes and, like the Frank system is also a corrected orthogonal lead system. Like the Frank system, the McFee system employs a resistance network for normalizing the signals generated.

Figure 3:
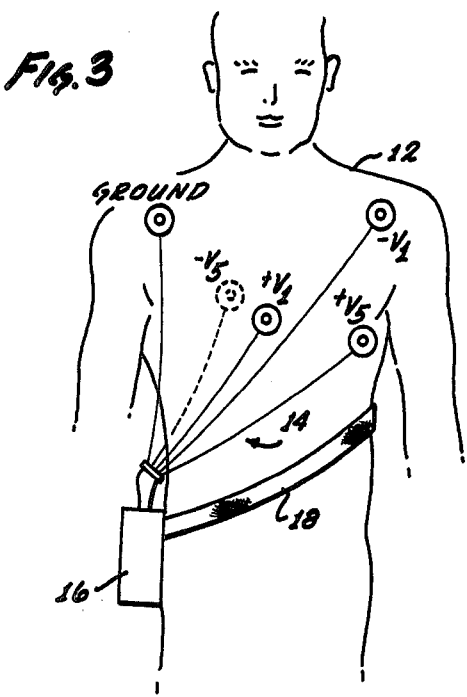
FIG. 3 is a diagram showing the placement of the electrodes in the present invention.

The lead system used in a preferred embodiment of the present invention is shown in FIG. 3. In contrast to the Frank and McFee systems illustrated in FIGS. 1 and 2 respectively, the lead system of the present invention employs only five electrodes. Because fewer electrodes are used, set-up time is reduced, patient apprehension is minimized, and the probability of a defective skin contact is materially reduced.

Figure 4:
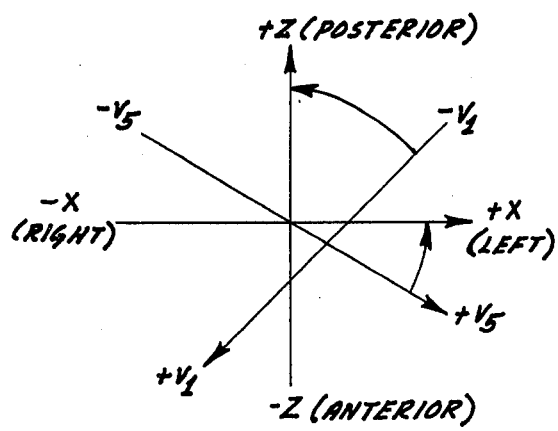
FIG. 4 is a diagram showing the projection of the $V_1$ and $V_5$ axes onto the horizontal (X-Z) plane.
Figure 5:
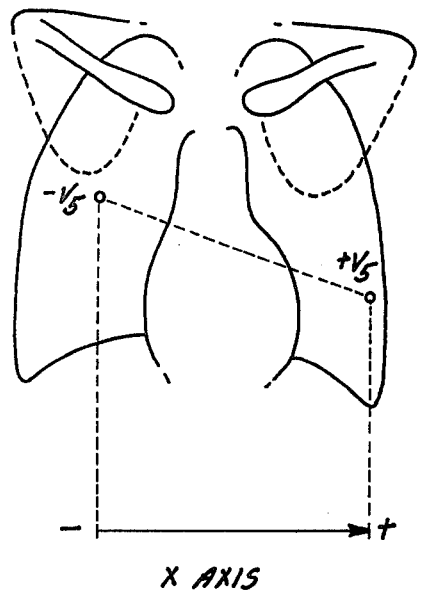
FIG. 5 is a diagram showing the projection of the $V_5$ axis onto the frontal plane.

The chest bipolar lead $V_5$ is so oriented as to be able to measure the X axis vector forces of the horizontal plane with the correct polarity, as may be seen from the coordinate diagram of FIG. 4. FIG. 5 is a frontal plane view showing the $V_5$ lead in its frontal projection.

Figure 6:
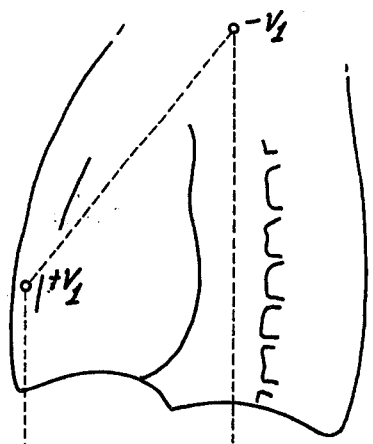
FIG. 6 is a diagram showing the projection of the modified $V_1$ axis onto the left sagittal plane.

Likewise, the modified chest bipolar lead $V_1$, with the negative electrode placed just inferior to the outer one-third of the clavicle, as shown in the sagittal view of FIG. 6, provides a measurement of the electrocardiagraphic signals in the direction of the Z axis of the horizontal plane, as shown in FIG. 4. However, the polarity of the modified chest lead $V_1$ must be reversed to render the sense of the signals the same as that used in the coordinate system. Thus, as viewed in the horizontal plane of FIG. 4, the $V_1$ and $V_5$ axes are approximately orthogonal, but are rotated with respect to the X and Z axes. It has been discovered that the signals provided by the lead system of FIG. 3, even though rotated as shown in FIG. 4, can be used to produce a horizontal plane vectorcardiogram which correlates to a high degree with horizontal plane vectorcardiograms obtained by use of the more complicated Frank lead system.

Figure 7:
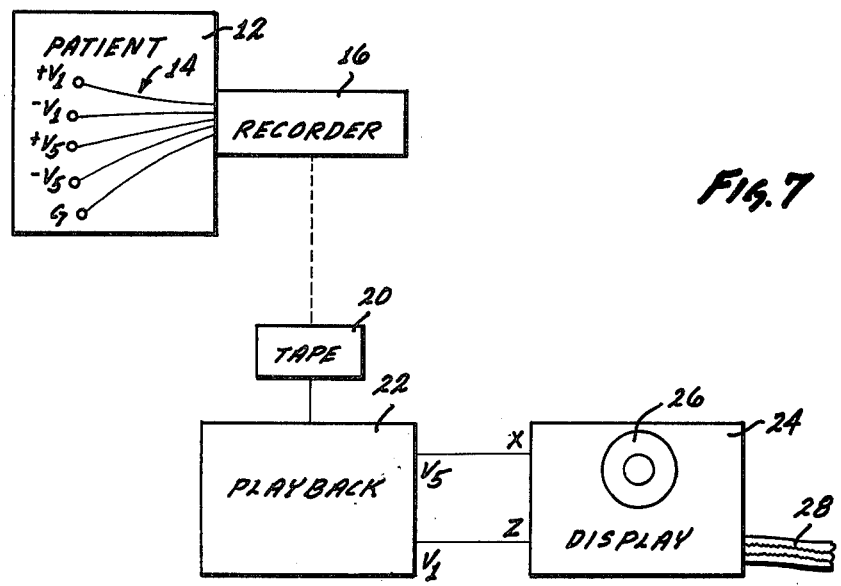
FIG. 7 is a block diagram of the apparatus used in a preferred embodiment of the present invention; and, FIG. 8 is a flow diagram showing the steps employed in a preferred embodiment of the present invention.

The apparatus used in practicing the present invention is shown in FIG. 7 in block diagram form. The five electrodes, $\pm V_1$, $\pm V_5$, and G are affixed to the patient 12 at the locations discussed above in connection with FIG. 3. Conductors 14 from these electrodes are connected to the recording inputs of the recorder 16, which is attached to the patient 12 by a belt 18 as shown in FIG. 3.

In a preferred embodiment, the recorder 16 is a Model 445 Holter Recorder produced by the assignee of the present invention, Del Mar Avionics of Irvine, California. That Recorder is disclosed in the co-pending application Ser. No. 717,651 filed Aug. 25, 1976 and entitled "Electrocardiographic Computer", and the description of that application is incorporated herein by reference.

The recorder 16 of the present invention is capable of recording simultaneously two channels of input data, such as $V_1$ and $V_5$, continuously over intervals in excess of 24 hours. The two channels of data are recorded in two separate tracks on the same magnetic tape 20.

The recorder 16 operates from a self-contained power supply so that after the recorder and electrodes have been attached, the patient 12 can go about his daily activities with a minimum of restriction. These daily activities may include periods of exercise which are designed to stress the patient's heart. The Model 445 Recorder used in the preferred embodiment further includes apparatus to permit the patient to place a marker signal on the tape at will, to indicate the times at which he experiences unusual heart sensations. During later analysis, the portions of the recording flagged by a marker signal can be readily located for detailed analysis.

As indicated by the dashed lines in FIG. 7, the tape 20 is removed from the recorder 16 following the recording interval and placed into the playback unit 22.

In a preferred embodiment, the playback unit 22 is a Model 660 Electrocardioscanner available from Del Mar Avionics in Irvine, Calif. The Model 660 Electrocardioscanner has been described in the above-referenced U.S. patent application Ser. No. 717,651, and that description is incorporated herein by reference.

As described in those patent applications, the Model 660 Electrocardioscanner includes provision for playing back the tape at any one of several speeds to reproduce the $V_1$ and $V_5$ signals from the tape 20. The Electrocardioscanner further includes provision for recognizing the occurrence of the marker signal on the tape so that the portions of the recording marked by the patient can be quickly found and identified.

Polarity reversal of the modified chest lead $V_1$ to conform to the direction of the Z axis (as discussed above) is accomplished by use of the ECG polarity switch of the appropriate channel of the Electrocardioscanner. The electrical signals $V_1$ and $V_5$ produced by the playback unit 22 are then fed to the display unit 24 as the X and Z inputs.

In a preferred embodiment, the display unit 24 includes a cathrode-ray oscilloscope 26 for displaying the vectorcardiogram. In one embodiment, the display unit 24 is a Model VCG-1B Vectorcardiograph available from Instruments for Cardiac Research, Inc., Syracuse, N.Y. In other embodiments, the display unit includes apparatus for producing a chart 28 of the X and Z inputs versus time. Such a chart 28 has proven to be a useful adjunct to the vector display shown on the oscilloscope 26. In still other embodiments, the display unit 24 is provided with a camera (not shown) for use in photographing the vector produced on the oscilloscope 26.

To insure uniform data reproduction, a sinusoidal 1.0 millivolt calibration signal is applied as an input to the recorder 16 to both the $V_1$ and $V_5$ channels simultaneously. Upon playback of the tape 20, the calibration signals are applied as the X and Z inputs to the display unit 24. The gain in each channel can then be adjusted to equalize the outputs on the chart 28. The display on the oscilloscope 26 produced by the calibration signals would normally be a straight line inscribed at 45°. If the two channels are out of phase, as might happen if the recording and playback heads are not accurately aligned, the calibration trace of the oscilloscope 26 will show an elliptical shape in general.

Figure 8:
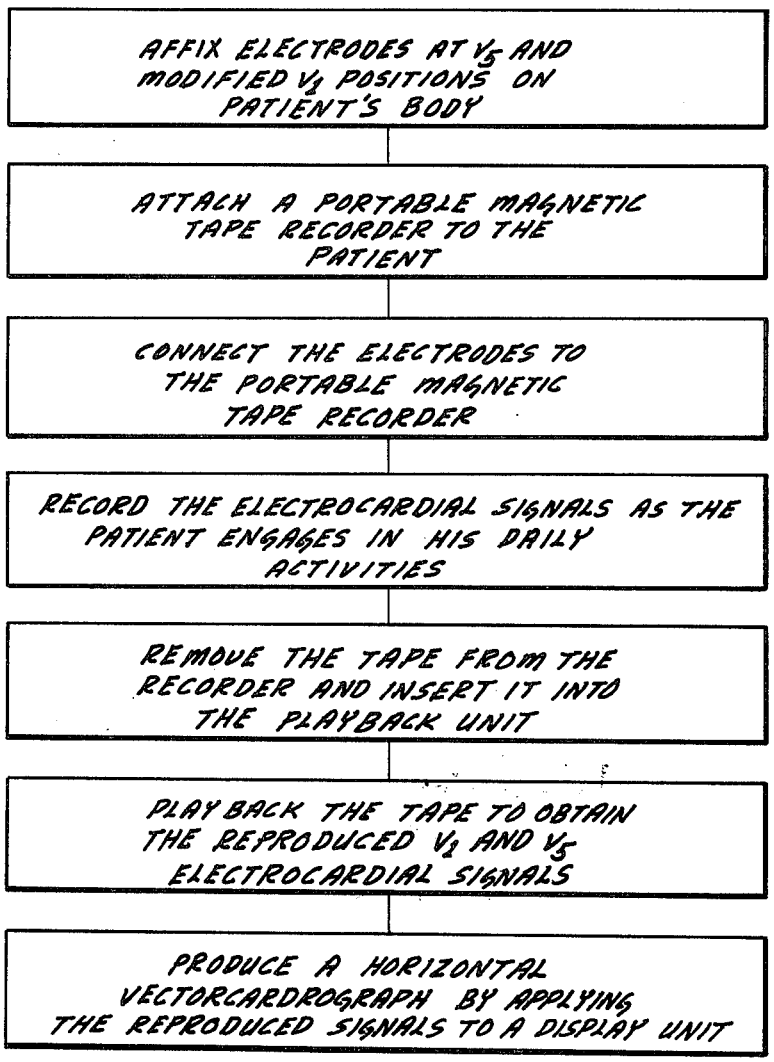

The method of the present invention is summarized in the flow diagram of FIG. 8.

In one embodiment of the method, the tape is played back at high speed to permit rapid scanning of the tape for anomalies in the vectorcardiogram. The anomalies can then be studied in detail by playing back the tape at a reduced speed. The vectorcardiograms exhibit high correlation with those obtained by use of the more common, but more complex, Frank lead system.

Numerous variations of the method and apparatus described above will be apparent to those skilled in the art. Those variations are included within the scope of the present invention which is limited only by the following claims.

What is claimed is:

1. A method of obtaining a horizontal vectorcardiogram from an ambulatory patient, comprising the steps of:
    (a) affixing electrodes at predetermined positions on the patient's body to pick up electrocardiac signals of the ambulatory patient;
    (b) attaching a portable magnetic tape recorder to the patient;
    (c) connecting the electrodes to the portable magnetic tape recorder;
    (d) recording on separate tracks in a magnetic recording tape inserted in the portable magnetic tape recorder the electrocardiac signals picked up by the electrodes as the patient engages in his daily activities;

(e) removing the magnetic recording tape from the portable magnetic tape recorder and inserting it into a playback apparatus;

(f) playing back the magnetic recording tape to produce two simultaneous reproduced electrocardiac electrical signals;

(g) producing a horizontal vectorcardiogram by applying the two simultaneous reproduced electrocardiac electrical signals to orthogonal inputs of a display unit.

2. The method of claim 1 wherein the electrodes are affixed to the ambulatory patient at the $V_5$ and modified $V_1$ positions.

3. The method of claim 1 wherein the recording step is continued for an interval in excess of one hour.

4. The method of claim 1 wherein the playing back step further comprises playing back the magnetic recording tape at a speed other than the speed at which it was recorded.

5. The method of claim 4 wherein the playback speed is faster than the speed at which the tape was recorded.

6. The method of claim 1 wherein the display unit includes a cathode-ray tube.

7. The method of claim 1 further comprising the step, following step (f), of:

producing charts of the two simultaneous reproduced electrocardiac electrical signals versus time, by use of a plotter.

* * * * *